United States Patent [19]

Childers, Jr. et al.

[11] Patent Number: 5,508,401

[45] Date of Patent: Apr. 16, 1996

[54] SUBSTITUTED DIBENZO[A,D]CYCLOHEPTENE NMDA ANTAGONISTS

[75] Inventors: Wayne E. Childers, Jr., Yardley; Magid A. Abou-Gharbia, Glen Mills; Edward J. Podlesny, New Tripoli, all of Pa.

[73] Assignee: American Home Products Corporation, Madison, N.J.

[21] Appl. No.: 658,283

[22] Filed: Feb. 20, 1991

[51] Int. Cl.$^6$ .................................................. C07D 487/08
[52] U.S. Cl. ............................................................. 540/581
[58] Field of Search ............................... 540/581; 514/214

[56] References Cited

U.S. PATENT DOCUMENTS

| 3,509,158 | 4/1970 | Dobson et al. | 540/581 |
| 3,597,433 | 8/1971 | Dobson et al. | 540/581 |
| 4,940,789 | 7/1990 | Childers, Jr. et al. | 540/581 |
| 5,011,834 | 4/1991 | Weber et al. | 514/212 |

FOREIGN PATENT DOCUMENTS 2148  4/1967  South Africa.

OTHER PUBLICATIONS

Brooks et al., J. Chem. Soc., Perkin I, 2588–2591 (1973).

Takayama et al., Chemistry Lett., 865–866 (1978).

*Primary Examiner*—Jyothsan Venkat
*Attorney, Agent, or Firm*—Richard K. Jackson

[57] ABSTRACT

This invention involves novel neuroprotectant agents of the formula:

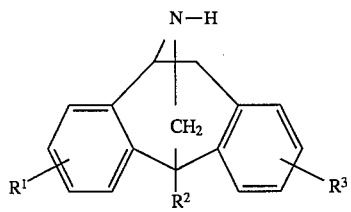

in which $R^1$ and $R^3$ are, independently, hydrogen, cyano, nitro, halo or perhaloalkyl, with the proviso that one of $R^1$ and $R^3$ is other than hydrogen; $R_2$ is alkyl; or a pharmaceutically acceptable salt thereof.

6 Claims, No Drawings

SUBSTITUTED DIBENZO[A,D] CYCLOHEPTENE NMDA ANTAGONISTS

BACKGROUND OF THE INVENTION

Antagonism of the centrally-acting excitatory amino acids (EAA), especially at the N-methyl-D-aspartate (NMDA)—specific receptor complex, is believed to represent a useful approach to the treatment of several CNS disorders, including senile dementia, Alzheimer's disease, Huntingdon's chorea, stroke, hypoglycemia, cerebral palsy, cerebral ischemia, epilepsy, and olivo-ponto-cerebellar atrophy. Two approaches to NMDA-antagonism have been pursued in recent years, namely competitive antagonism of the NMDA receptor and noncompetitive blockade of the NMDA-associated ion channel. To date, noncompetitive antagonists have proved more potent and more orally active than their competitive counterparts in blocking NMDA-induced responses in vivo and in protecting against cell death associated with induced cerebral ischemia.

Data suggest that phencyclidine (PCP) and other related "dissociative anesthetics" noncompetitively antagonize NMDA-induced responses by binding to the NMDA-associated ion channel and blocking ion permeability. Unfortunately, PCP possesses undesirable psychotomimetic side effects and causes ataxia in several animal models. In fact, the separation between a compound's NMDA-antagonist activity and ataxic activity (often expressed as an "efficacy ratio" of the $ED_{50}$'s of these two activities) has been extensively used to evaluate its therapeutic usefulness versus its liabilities. In our studies, PCP is approximately equipotent in its abilities to antagonize NMDA-induced lethality in mice and cause ataxia as measured by the traction reflex deficit model, giving an efficacy ratio ($ED_{50}/TD_{50}$) of approximately 1.4 (Table 1, infra).

A very potent noncompetitive NMDA-antagonist reported recently is MK-801. Like PCP, MK-801 antagonizes NMDA-induced lethality and protects against cell death in cerebral ischemia models. However, MK-801 competes for the high-affinity PCP binding site in the NMDA-associated ion channel. Furthermore, like PCP, them is no separation between MK-801's ability to antagonize NMDA-induced lethality and cause ataxia (efficacy ratio=0.9, Table 1 infra). In fact, in drug discrimination experiments, MK-801 generalizes for PCP, suggesting that MK-801 may possess PCP-like psychotomimetic side effects.

Dextromethorphan, an over-the-counter antitussive, also noncompetitively antagonizes NMDA-induced responses (Table 1, infra). Its proposed binding site in the ion channel may be different from that shared by PCP and MK-801. While not as potent as PCP and MK-801 in antagonizing NMDA-induced lethality, dextromethorphan shows a better antagonism/ataxia efficacy ratio (2.1). However, dextromethorphan is metabolized to dextrorphan in man. Dextrorphan's efficacy ratio is essentially the same as that for dextromethorphan, but data suggests that dextrorphan may exert its effects by interacting with the high-affinity PCP binding site in the NMDA-associated ion channel. This fact again raises the question of PCP-like psychotomimetic side effects.

DESCRIPTION OF THE INVENTION

In accordance with this invention, there is provided a group of novel compounds which because of their CNS activity profile are considered to be useful in the treatment of neurodegenerative diseases such as Alzheimer's disease, Huntingdon's chorea, senile dementia, Parkinson's syndrome, and olivo-ponto-cerebellar atrophy, as well as epilepsy, stroke, hypoglycemia, cerebral palsy, cerebral ischemia and anxiety. Surprisingly, these compounds are intermediates useful in the production of the neuroprotectant agents disclosed in our earlier patent, U.S. Pat. No. 4,940,789.

Compounds of the present invention are described by the generic formula:

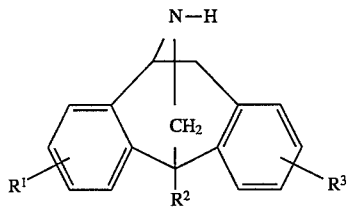

in which
$R^1$ and $R^3$ are, independently, hydrogen, cyano, nitro, halo or perhaloalkyl of 1 to 6 carbon atoms, with the proviso that one of $R^1$ and $R^3$ is other than hydrogen;
$R_2$ is alkyl of 1 to 6 carbon atoms;
or a pharmaceutically acceptable salt thereof.

Preferred neuroprotectants from the standpoint of production economics and activity profile are those of the formula:

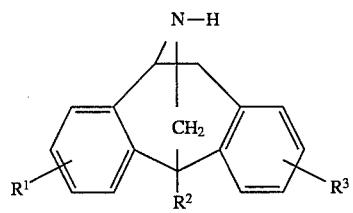

in which
one of $R^1$ and $R^3$ is hydrogen and the other is —CN, —$NO_2$, —Cl, —Br—, —F, —I or —$CF_3$;
$R^2$ is alkyl of 1 to 3 carbon atoms;
or a pharmaceutically acceptable salt thereof.

The pharmaceutically acceptable salts of the compounds of this invention are prepared conventionally from organic or inorganic acids such as acetic, lactic, citric, tartaric, succinic, maleic, malonic, gluconic, hydrochloric, hydrobromic, phosphoric, nitric, sulfuric, methanesulfonic, and similarly known acceptable acids.

The compounds of this invention may be prepared via a variety of routes using conventional methods and commercially available starting materials. Thus, the desired substituted 10,11-dihydro-5-alkyl- 10,5-(iminomethano)-5H-dibenzo[a,d]cycloheptenes can be prepared from appropriately substituted 1,2-diphenylethylamines using the methods of R. D. Waigh, et al., J. Chem. Soc., Perkin I (1973), 2588, and H. Takayama, et al., Chem. Lett.(1978), 865, employing a suitably substituted propargyl halide and a suitable base such as diisopropylethylamine followed by treatment with a suitable non-aqueous acid such as trifluoromethanesulfonic acid.

The compounds of this invention are chiral, having an assymetric center at the 5- and 10-positions. As such, they appear as racemic mixtures which may be resolved into their optical isomers by routine methods within the skill of the medicinal chemist. Also, the desired isomer may be obtained by stereospecific synthesis employing the desired isomeric reactant form.

The following examples illustrate, without limitation, the preparation of representative compounds of this invention.

EXAMPLE 1

10,11-Dihydro-3-bromo-5-methyl-10,5-(iminomethano)-5H-dibenzo[a,d]cycloheptene

A stirred solution of 1-phenyl-2-(4-bromophenyl)ethylamine (4.37 g, $1.6 \times 10^{-2}$ mol), propargyl bromide (80% in toluene, 3.10 g, $2.1 \times 10^{-2}$ mol), and diisopropylethylamine (3.07 g, $2.4 \times 10^{-2}$ mol) in 120 ml of anhydrous tetrahydrofuran was refluxed at 90° C. under a dry nitrogen atmosphere for three hours. Then, an additional portion of propargyl bromide (0.59 g, $4.0 \times 10^{-3}$ mol) was added, and reflux was continued for another two hours. The reaction mixture was cooled to room temperature, and the resulting white precipitate was removed by filtration. The mother liquor was concentrated on a rotary evaporator, the residue was diluted with 200 ml of diethyl ether, and the resulting white precipitate was again removed by filtration. The etheral mother liquor was quickly extracted with two 75 ml portions of 2N aqueous HCl. Upon standing, the combined aqueous layers yielded the desired intermediate, N-propargyl-1-phenyl-2-(4-bromophenyl)ethylamine hydrochloride, as a yellow precipitate which was recrystallized from ethanol/diethyl ether (4.54 g, 81%), mp=197°–199° C.

A solution of N-propargyl-1-phenyl-2-(4-bromophenyl)ethylamine hydrochloride (4.47 g, $1.3 \times 10^{-2}$ mol) in trifluoromethanesulfonic acid (20 g, $1.3 \times 10^{-1}$ mol) was allowed to stand at room temperature under a dry nitrogen atmosphere for 18 hours. The reaction mixture was then poured onto ice, and the pH of the aqueous mixture was adjusted to 10 with 50% aqueous NaOH. The resulting basic mixture was diluted to 200 ml with water and extracted three times with 100 ml portions of chloroform. The combined organic layers were dried over anhydrous sodium sulfate and concentrated on a rotary evaporator. The title compound (TLC on silica gel using a 5% methanol in methylene chloride solvent system, Rf=0.26) was isolated by preparative HPLC on silica gel using a gradient of 50% methylene chloride in ethyl acetate to 20% methanol in ethyl acetate. It was then converted to the HCl salt with isopropanolic HCl (2.67 g, 59%), mp=321°–322° C.
Elemental analysis for $C_{17}H_{16}NBr \cdot HCl \cdot \frac{1}{16}H_2O$
  Calc'd: C, 58.04; H, 4.90; N, 3.98
  Found: C, 57.75; H, 4.58; N, 3.92

EXAMPLE 2

10,11-Dihydro-7-bromo-5-methyl-10,5-(iminomethano)-5H-dibenzo[a,d]cycloheptene

A stirred solution of 1-(4-bromophenyl)-2-phenylethylamine (4.76 g, $1.72 \times 10^{-2}$ mol), propargyl bromide (80% in toluene, 3.47 g, $2.33 \times 10^{-2}$ mol), and diisopropylethylamine (3.41 g, $2.64 \times 10^{-2}$ mol) in 125 ml of anhydrous tetrahydrofuran was refluxed at 90° C. under a dry nitrogen atmosphere for three hours. Then, an additional portion of propargyl bromide (1.34 g, $9.0 \times 10^{-3}$ mol) was added, and reflux was continued for another two hours. The reaction mixture was cooled to room temperature, and the resulting white precipitate was removed by filtration. The mother liquor was concentrated on a rotary evaporator, the residue was diluted with 250 ml of diethyl ether, and the resulting white precipitate was again removed by filtration. The etheral mother liquor was quickly extracted with two 100 ml portions of 2N aqueous HCl. Upon standing, the combined aqueous layers yielded the desired intermediate, N-propargylol-1-(4-bromophenyl)-2-phenylethylamine hydrochloride, as an orange precipitate which was recrystallized from ethanol/diethyl ether (4.47 g, 74%), mp=164°–165° C.

A solution of N-propargyl-1-(4-bromophenyl)-2-phenylethylamine hydrochloride (4.30 g, $1.22 \times 10^{-2}$ mol) in trifluoromethanesulfonic acid (36 g, $2.5 \times 10^{-1}$ mol) was allowed to stand at 50° C. under a dry nitrogen atmosphere for 24 hours. The reaction mixture was then poured onto ice, and the pH of the aqueous mixture was adjusted to 10 with 50% aqueous NaOH. The resulting basic mixture was diluted to 400 ml with water and extracted three times with 200 ml portions of chloroform. The combined organic layers were dried over anhydrous sodium sulfate and concentrated on a rotary evaporator. The title compound (TLC on silica gel using a 5% methanol in methylene chloride solvent system, Rf=0.26) was isolated by preparative HPLC on silica gel using a gradient of 50% methylene chloride in ethyl acetate to 20% methanol in ethyl acetate. A 1.0 g sample of the free base was then converted to the HCl salt with isopropanolic HCl (0.93 g, 59%), mp=309°–311° C.
Elemental analysis for $C_{17}H_{16}NBr \cdot HCl$
  Calc'd: C, 58.23; H, 4.89; N, 3.99
  Found: C, 57.30; H, 5.06; N, 3.78

EXAMPLE 3

10,11-Dihydro-3-chloro-5-methyl-10,5-(iminomethano)-5H-dibenzo[a,d]cycloheptene

A stirred solution of 1-phenyl-2-(4-chlorophenyl)ethylamine (6.00 gm, $2.6 \times 10^{-2}$ mol), propargyl bromide (80% in toluene, 4.82 gm, $3.2 \times 10^{-2}$ mol), and diisopropylethylamine (5.04 gm, $3.9 \times 10^{-2}$ mol) in 50 ml of anhydrous tetrahydrofuran was refluxed at 90° C. under a dry nitrogen atmosphere for four hours. Then, an additional portion of propargyl bromide (0.48 gm, $3.9 \times 10^{-3}$ mol) was added, and reflux was continued to another two hours. The reaction mixture was cooled to room temperature, and the resulting white precipitate was removed by filtration. The mother liquor was concentrated on a rotary evaporator, the residue was diluted with 100 ml of diethyl ether, and the resulting white precipitate was again removed by filtration. The etheral mother liquor was quickly extracted with two 50 ml portions of 2N aqueous HCl. Upon standing, the combined aqueous layers yielded the desired intermediate, N-propargyl-1-phenyl-2-(4-chlorophenyl)ethylamine hydrochloride, as an off-white precipitate, which was washed with diethyl ether (4.53 gm, 57%), mp=191°–193°.

A solution of N-propargyl-1-phenyl-2-(4-chlorophenyl)ethylamine hydrochloride (4.40 gm, $1.4 \times 10^{-2}$ mol) in trifluoromethanesulfonic acid (22 gm, $1.4 \times 10^{-1}$ mol) was allowed to stand under a dry nitrogen atmosphere for 24 hours. The reaction mixture was then poured onto ice and the pH of the aqueous mixture was adjusted to 10 with 50% aqueous sodium hydroxide. The resulting basic mixture was diluted to 200 ml with water and extracted 3 times with 100 ml portions of dichloromethane. The combined organic layers were dried over anydrous sodium sulfate and concentrated on a rotary evaporator. The title compound (TLC on silica gel using a 5% methanol in methylene chloride solvent system, Rf = 0.21) was isolated using column chromatography on silica gel by first eluting with 1% methanol/dichloromethane and then with 10% methanol/dichloromethane. The amine was then converted to its hydrochloride salt with isopropanolic HCl (1.80 gm, 41%), mp=308°–310° C.
Elemental analysis for $C_{17}H_{16}NCl \cdot HCl$
  Calc'd: C, 66.68; H, 5.60; N, 4.57
  Found: C, 66.68; H, 5.62; N, 4.38

EXAMPLE 4

10,11-Dihydro-3-fluoro-5-methyl-10,5-(iminomethano)-5H-dibenzo[a,d]cycloheptene

A stirred solution of 1-phenyl-2-(4-fluorophenyl)ethylamine (5.60 gm, $2.6\times10^{-2}$ mol), propargyl bromide (80% in toluene, 4.82 gm, $3.2\times10^{-2}$ mol), and diisopropylethylamine (5.04 gm, $3.9\times10^{-2}$ mol) in 50 ml of anhydrous tetrahydrofuran was refluxed at 90° C. under a dry nitrogen atmosphere for four hours. Then, an additional portion of propargyl bromide (0.48 gm, $3.9\times10^{-3}$ mol) was added, and reflux was continued for another two hours. The reaction mixture was cooled to room temperature, and the resulting white precipitate was removed by filtration. The mother liquor was concentrated on a rotary evaporator, the residue was diluted with 100 ml of diethyl ether, and the resulting white precipitate was again removed by filtration. The etheral mother liquor was quickly extracted with two 50 ml portions of 2N aqueous HCl. Upon standing, the combined aqueous layers yielded the desired intermediate. N-propargyl-1-phenyl-2-(4-fluorophenyl)ethylamine hydrochloride, as an off-white precipitate, which was washed with diethyl ether (3.70 gm, 49%), mp=190°–191° C.

A solution of N-propargyl-1-phenyl-2-(4-fluorophenyl)ethylamine hydrochloride (3.09 gm, $1.07\times10^{-2}$ mol) in trifluoromethanesulfonic acid (16 gm, $1.07\times10^{-1}$ mol) was allowed to stand under a dry nitrogen atmosphere for 24 hours. The reaction mixture was then poured onto ice and the pH of the aqueous mixture was adjusted to 10 with 50% aqueous sodium hydroxide. The resulting basic mixture was diluted to 200 ml with water and extracted 3 times with 100 ml portions of dichloromethane. The combined organic layers were dried over anhydrous sodium sulfate and concentrated on a rotary evaporator. The title compound (TLC on silica gel using a 5% methanol in methylene chloride solvent system, Rf=0.20) was isolated using column chromatography on silica gel by first eluting with 1% methanol/dichloromethane and then with 10% methanol/dichloromethane. The amine was then converted to its hydrochloride salt with isopropanolic HCl (1.34 gm, 43%), mp=321°–323° C.

Elemental analysis for $C_{17}H_{16}NF.HCl$
Calcd: C, 70.46; H, 5.25; N, 4.88
Found: C, 70.07; H, 5.39; N, 4.89

EXAMPLE 5

(-)-10,11-Dihydro-3-bromo-5-methyl-10,5-(iminomethano)-5H-dibenzo[a,d]cycloheptene 1-phenyl-2-(4-bromophenyl)ethylamine (5.48 g, $1.98\times10^{-2}$ mol) was dissolved in 20 ml of 10% ethyl acetate/ethanol. To this was added a solution of R(+)-α-methoxy-α-(trifluoromethyl)phenylacetic acid (4.65 gm, $1.98\times10^{-2}$ mol) in 20 ml of 10% ethyl acetate/ethanol. The resulting solution was warmed to 75° C., and then allowed to stand at room temperature for 72 hours. The mixture was then left in the freezer for 24 hours. The resulting white precipitate was collected by vacuum filtration, washed with diethyl ether, and dried in vacuo to yield the desired (+)-α-methoxy-α-(trifluoromethyl)phenyl acetate of (+)-1-phenyl-2-(4-bromophenyl)ethylamine (1.49 gm, 29%), mp=144°–146° C. The salt was treated with 30 ml of 2.5N aqueous NaOH, extracted with three 30 ml portions of dichloromethane, and the combined organic layers were dried over anhydrous sodium sulfate and concentrated on a rotary evaporator to yield the desired (+)-1-phenyl-2-(4-bromophenyl)ethylamine as a yellow oil (0.62 gm, 23% yield), $[\alpha]_D^{25}=+58.3$ (EtOH), shown to be 99.9% enantiomerically pure by chiral HPLC.

A stirred solution of (+)-1-phenyl-2-(4-bromophenyl)ethylamine (0.62 gm, $2.2\times10^{-3}$ mol), propargyl bromide (80% in toluene, 0.58 gm, $4.9\times10^{-3}$ mol), and diisopropylethylamine (0.61 gm, $4.7\times10^{-3}$ mol) in 10 ml of anhydrous tetrahydrofuran was refluxed at 90° C. under a dry nitrogen atmosphere for four hours. The reaction mixture was cooled to room temperature, and the mother liquor was concentrated on a rotary evaporator. The residue was diluted with 30 ml of diethyl ether, and the resulting white precipitate was removed by filtration. The etheral mother liquor was quickly extracted with 30 ml of 2N aqueous HCl. Upon standing, the combined aqueous layers yielded the desired intermediate, (+)-N-propargyl-t-phenyl-2-(4-bromophenyl)ethylamine hydrochloride, as a yellow precipitate, which was washed with ethyl ether (0.69 gm, 89%), mp=205°–207° C., $[\alpha]_D^{25}=+68.7$ (EtOH).

A solution of (+)-N-propargyl-1-phenyl-2-(4-bromophenyl)ethylamine hydrochloride (0.63 gm, $1.8\times10^{-3}$ mol) in trifluoromethanesulfonic acid (2.7 gm, $1.8\times10^{-2}$ mol) was allowed to stand under a dry nitrogen atmosphere for 24 hours. The reaction mixture was then poured onto ice and the pH of the aqueous mixture was adjusted to 10 with 50% aqueous sodium hydroxide. The resulting basic mixture was diluted to 50 ml with water and extracted 3 times with 20 ml portions of dichloromethane. The combined organic layers were dried over anhydrous sodium sulfate and concentrated on a rotary evaporator. The title compound (TLC on silica gel using a 5% methanol in methylene chloride solvent system, Rf=0.21) was isolated using column chromatography on silica gel by first eluting with 1% methanol/dichloromethane and then with 10% methanol/dichloromethane. The amine was then converted to its hydrochloride salt with isopropanolic HCl (0.30 gm, 49% ), mp=312°–314° C., $[\alpha]_D^{25}=-239.2$ (EtOH).

Elemental analysis for $C_{17}H_{16}NBr.HCl$
Calc'd: C, 58.22; H, 4.89; N, 3.99
Found: C, 58.16; H, 4.96; N, 3.85

EXAMPLE 6

(+)-10,11-Dihydro-3-bromo-5-methyl-10,5-(iminomethano)-5H-dibenzo[a,d]cycloheptene 1-Phenyl-2-(4-bromophenyl)ethylamine (6.71 gm, $2.43\times10^{-2}$ mol) was dissolved in 40 ml of 25% ethyl acetate/ethanol. This solution was then added to a solution of S(-)-α-methoxy-α-(trifluoromethyl)phenylacetic acid (5.69 gm, $2.43\times10^{-2}$ mol) in 40 ml of 25% ethyl acetate/ethanol. The resulting solution was warmed to 60° C., and then allowed to stand at room temperature for 116 hours. The mixture was then left in a freezer for 24 hours. The resulting white precipitate was collected by vacuum filtration, washed with ethyl ether, and dried in vacuo to yield the desired (-)-α-methoxy-α-trifluoromethyl)phenyl acetate of (-)-1-phenyl-2-(4-bromophenyl)ethylamine (2.93 gm). The mother liquor was concentrated to dryness under reduced pressure, and the residue was crystallized as described above using 60 ml of 25% ethyl acetate/ethanol to yield an additional 0.63 gm of the phenylacetate of (-)-1-phenyl-2-(4-bromophenyl)ethylamine. The combined precipitates (3.56 gm, 57%, mp=143°–145° C.) were treated with 30 ml of 2.5N aqueous NaOH, extracted with three 30 ml portions of dichloromethane, and the combined organic layers were dried over anhydrous sodium sulfate and concentrated on a rotary evaporator to yield the desired (-)-1-phenyl-2-(4-bromophenyl)ethylamine as a yellow oil (1.74 gm, 52%), $[\alpha]_D^{25}=-62.7$ (EtOH), shown to be 99.8% enantiomerically pure by chiral HPLC.

A stirred solution of (-)-1-phenyl-2-(4-bromophenyl)ethylamine (2.06 gm, 7.5×10$^{-3}$ mol), propargyl bromide (80% in toluene, 1.66 gm, 11.2×10$^{-3}$ mol), and diisopropylethylamine (1.45 gm, 16.2×10$^{-3}$ mol) in 20 ml of anhydrous tetrahydrofuran was refluxed at 90° C. under a dry nitrogen atmosphere for five hours. The reaction mixture was cooled to room temperature, and the mother liquor was concentrated on a rotary evaporator. The residue was diluted with 75 ml of diethyl ether, and the resulting white precipitate was removed by filtration. The etheral mother liquor was quickly extracted with 50 ml of 2N aqueous HCl. Upon standing, the combined aqueous layers yielded the desired intermediate, (-)-N-propargyl-1-phenyl-2-(4-chlorophenyl)ethylamine hydrochloride, as a yellow precipitate, which was washed with ethyl ether (1.25 gm, 48%), mp=212°–213° C., $[\alpha]^{25}_D=-69.7$ (EtOH).

A solution of (-)-N-propargyl-1-phenyl-2-(4-bromophenyl)ethylamine hydrochloride (1.16 gm, 3.3×10$^{-3}$ mol) in trifluoromethanesulfonic acid (5.0 gm, 3.3× 10$^{-2}$ mol) was allowed to stand under a dry nitrogen atmosphere for 24 hours. The reaction mixture was then poured onto ice and the pH of the aqueous mixture was adjusted to 10 with 50% aqueous sodium hydroxide. The resulting basic mixture was diluted to 75 ml with water and extracted 4 times with 50 ml portions of chloroform. The combined organic layers were dried over anhydrous sodium sulfate and concentrated on a rotary evaporator. The title compound (TLC on silica gel using a 5% methanol in methylene chloride solvent system, Rf=0.21) was isolated using column chromatography on silica gel by first eluting with 1% methanol/dichloromethane and then with 10% methanol/dichloromethane. The amine was then converted to its hydrochloride salt with isopropanolic HCl (0.67 gm, 58%), mp=314°–316° C., $[\alpha]^{25}_D=+237.9$ (EtOH).

Elemental analysis for $C_{17}H_{16}NBr \cdot HCl$

Calc'd: C, 58.22; H, 4.89; N, 3.99

Found: C, 57.99; H, 4.97; N, 3.84

The properties of these compounds were directly established by demonstrating the NMDA antagonist properties of representative compounds in male Swiss-albino mice (CD-1 strain, Charles River) 18–22 grams in weight after 18 hours of food deprivation which had been habituated to an observation chamber for 30 minutes. The mice were pretreated with the representative test compounds followed thirty minutes later with NMDA (195 mg/kg, i.p., the ED$_{90}$ dose for generalized myoclonus). The mice were then observed for 30 minutes, noting the latency of onset of generalized myoclonus (uncontrollable hind leg scratching or limbs and/or torso muscle jerking with loss of fighting reflex) and death. From the latter, the ED$_{50}$ for survival is determined. In this standard experimental test procedure, the specific compounds tested and their activity, which representatively establish the activity for all the compounds herein, are presented in Table I as follows:

TABLE 1

NMDA-Induced Lethality and Traction Reflex Deficit (Ataxia)

| Compound Of Example | *ED$_{50}$ Inhibition of NMDA-Induced Lethality (mg/kg, ip) | @TD$_{50}$- Traction Reflex Deficit (mg/kg, ip) | Efficacy Ratio (ED$_{50}$/TD$_{50}$) |
|---|---|---|---|
| 1 | 4.6 | 14.7 | 3.2 |
| 2 | #60% (20) | | |
| 3 | #90% (5) | | |
| 4 | #90% (5) | | |
| 5 | #40% (5) | | |
| 6 | 2.2 | | |
| PCP | 1.9 | 2.7 | 1.4 |
| MK-801 | 0.19 | 0.17 | 0.9 |
| Dextromethorphan | 21 | 45 | 2.1 |
| Dextrorphan | 13 | 29 | 2.2 |

*As measured in mice. Defined as the dose required to produce 50% survival rate.
@As measured in mice. Defined as the dose which produced the deficit in 50% of animals tested.
Percent of animals which survived at the dose indicated.

In addition, the compounds involved herein were shown to displace 1-(2-thienyl)- 1-(1-piperidinyl)cyclohexane (TCP) from its binding site in the NMDA-associate ion channel in rat frontal cortex homogenates, by loading rat brain homogenate with radiolabeled TCP and subsequently measuring the amount of TCP displaced by the test compounds of this invention. The inhibitory concentration in nM which displaced 50% of the radiolabeled TCP was found to be as presented in Table 2.

TABLE 2

Ability to Displace [$^3$H]-TCP from the NMDA Ion Channel

| Compound of Example | *IC$_{50}$ (nM) |
|---|---|
| 1 | 192 |
| 2 | 110 |
| 5 | 1,010 |
| 6 | 89 |
| MK-801 | 2.6 |
| PCP | 28.2 |
| Dextromethorphan | 745 |

*Functional binding assay without added spermidine.

Thus, the compounds of this invention demonstrate the ability to antagonize NMDA-induced lethality in vivo in mice (Table 1). They did not compete with 3-( 2-carboxypiperazinyl-4-yl)-propyl-1-phosphonic acid (CPP), a known competitive NMDA-antagonist, for its binding site in rat frontal cortex homogenates. Compounds of the present invention displaced 1-(2-thienyl)-1-(1-piperidinyl)cyclohexane (TCP) from its binding site in the NMDA-associated ion channel in rat frontal cortex homogenates (Table 2) which characterizes them as noncompetitive NMDA antagonists. Compounds of the present invention also provide robust neuroprotection in a gerbil global ischemia model when given at a dose of 30 mg/kg i.p., 2×4 hours apart. The compounds of this invention showed efficacy ratios for antagonizing NMDA-induced lethality over ataxia superior to those seen with PCP, MK-801, dextrorphan, and dextromethorphan (Table 1). In addition, they demonstrated more potent neuroprotection (with less lethality) than dextrorphan, dextromethorphan, or the N-substituted derivatives disclosed in U.S. Pat. No. 4,940,789 which are not aryl-substituted.

The combination of oral activity, greater potency with respect to dextromethorphan and dextrorphan, and better efficacy ratios relative to standard NMDA antagonists, including PCP, MK-801, dextromethorphan, and dextrorphan, makes the compounds of this invention superior to presently available noncompetitive NMDA antagonists. Compounds with such a profile are useful in the treatment of CNS disorders such as senile dementia, Alzheimer's disease, Huntingdon's chorea, stroke, hypoglycemia, cerebral palsy, cerebral ischemia, epilepsy, and olivo-ponto cerebellar atrophy.

Hence, there is herewith provided in addition to the novel compounds, supra, a method for preventing neurodegenerative disorders induced by overstimulation of excitatory amino acid receptors in brain and spinal cord, which comprises administering to a mammal suffering from such degenerative disease states, an NMDA antagonist of the formula:

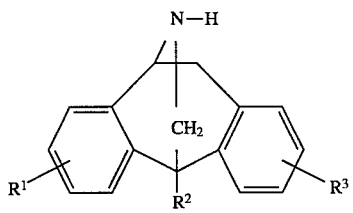

in which $R^1$ and $R^3$ are, independently, hydrogen, cyano, nitro, halo or perhaloalkyl of 1 to 6 carbon atoms, with the proviso that one of $R^1$ and $R^3$ is other than hydrogen;

$R_2$ is alkyl of 1 to 6 carbon atoms;

or a pharmaceutically acceptable salt thereof.

As such, the compounds of this invention may be administered neat or with a pharmaceutical carrier to a patient in need thereof. The pharmaceutical carrier may be solid or liquid.

A solid carrier can include one or more substances which may also act as flavoring agents, lubricants solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compounds can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

To determine the effective amount of compound to be administered in alleviation of CNS degenerative dysfunctions, the physician need only evaluate the effects of a given NMDA antagonist in the patient by incrementally increasing the oral dosage from about 1 mg/kg to about 20 mg/kg until the desired symptomatic relief level is achieved. The continuing dose regimen may then be modified to achieve the desired result, with the range of about 1 to 100 mg/day. Similar techniques are followed by determining the effective dose range upon i.v. or i.m. administration. When using the compounds prophylactically to arrest declining cognitive function as in Alzheimer's dementia, a more subjective approach is taken such as by relating the drug dosage to improved memory reponses or analogous desired responses which can be related to relief of overstimulation of the excitatory amino acid receptors.

What is claimed is:

1. A compound which is 10,11-dihydro-3-bromo-5-methyl-10,5-(iminomethano)-5H-dibenzo[a,d]cycloheptene, or a pharmaceutically acceptable salt thereof.

2. A compound which is 10,11-dihydro-7-bromo-5-methyl-10,5-(iminomethano)-5H-dibenzo[a,d]cycloheptene, or a pharmaceutically acceptable salt thereof.

3. A compound which is 10,11-dihydro-3-chloro-5-methyl-10,5 -(iminomethano)-5H-dibenzo[a,d]cycloheptene, or a pharmaceutically acceptable salt thereof.

4. A compound which is 10,11-dihydro-3-fluoro-5-methyl-10,5 -(iminomethano)-5H-dibenzo[a,d]cycloheptene, or a pharmaceutically acceptable salt thereof.

5. A compound which is (-)-10,11-dihydro-3-bromo-5-methyl-10,5 -(iminomethano)-5H-dibenzo[a,d]cycloheptene, or a pharmaceutically acceptable salt thereof.

6. A compound which is (+)-10,11-dihydro-3-bromo-5-methyl-10,5 -(iminomethano)-5H-dibenzo[a,d]cycloheptene, or a pharmaceutically acceptable salt thereof.

* * * * *